United States Patent [19]
Overby et al.

[11] 4,000,565
[45] Jan. 4, 1977

[54] DIGITAL AUDIO OUTPUT DEVICE

[75] Inventors: Albert W. Overby; Donald P. Parks, both of Cary, N.C.

[73] Assignee: International Business Machines Corporation, Armonk, N.Y.

[22] Filed: May 5, 1975

[21] Appl. No.: 574,828

[52] U.S. Cl. .............................. 35/35 A; 179/1 SA; 235/156; 179/1 SF; 358/94
[51] Int. Cl.² .................. G06K 9/00; H04M 1/00; G06F 7/38
[58] Field of Search ................. 35/35 A; 340/407; 178/DIG. 32; 179/1 SM, 2 DP, 19 A, 19 SF

[56] References Cited
UNITED STATES PATENTS

| | | | |
|---|---|---|---|
| 2,616,983 | 11/1952 | Zworykin et al. | 178/DIG. 32 X |
| 2,771,509 | 11/1956 | Dudley et al. | 179/1 SM |
| 3,059,064 | 10/1962 | Lebell | 35/35 A X |
| 3,114,980 | 12/1963 | Davis | 178/DIG. 32 X |
| 3,344,239 | 9/1967 | Ragland | 179/1 SM X |
| 3,356,836 | 12/1967 | Stenby | 235/151 |
| 3,398,241 | 8/1968 | Lee | 179/1 SM |
| 3,507,997 | 4/1970 | Weitbrecht | 179/2 DP |
| 3,632,887 | 8/1972 | Leipp et al. | 179/1 SF |
| 3,800,082 | 3/1974 | Fish | 178/DIG. 32 X |
| 3,828,252 | 8/1974 | Wolff | 324/99 D |
| 3,869,575 | 3/1975 | Spitz et al. | 179/1 SA |

*Primary Examiner*—Richard Murray
*Assistant Examiner*—Aristotelis M. Psitos
*Attorney, Agent, or Firm*—Edward H. Duffield

[57] ABSTRACT

An apparatus is disclosed for converting silent digital visual display characters into sequentially enunciated audible tones which are digitally coded in serial form. Blind or visually handicapped persons can recognize the audio tone codes to comprehend the visual characters in the optical display.

5 Claims, 8 Drawing Figures

| FIG. 1A | FIG. 1B | FIG. 1C | FIG. 1D |

FIG. 4

| CALCULATOR CHARACTER | INPUT PIN # | | | | | OUTPUT PIN # | | | | | |
|---|---|---|---|---|---|---|---|---|---|---|---|
| | A0 14 | A1 13 | A2 12 | A3 11 | A4 10 | B0 1 | B1 2 | B2 3 | B3 4 | B6 7 | B7 9 |
| 0 | 1 | 1 | 1 | 1 | 0 | 0 | 0 | 0 | 0 | 0 | 0 |
| 1 | 0 | 1 | 0 | 1 | 0 | 0 | 0 | 0 | 1 | 0 | 0 |
| 2 | 1 | 1 | 1 | 0 | 1 | 0 | 0 | 1 | 0 | 0 | 0 |
| 3 | 1 | 0 | 1 | 1 | 1 | 0 | 0 | 1 | 1 | 0 | 0 |
| 4 | 0 | 1 | 0 | 1 | 1 | 0 | 1 | 0 | 0 | 0 | 0 |
| 5 | 1 | 0 | 0 | 0 | 0 | 0 | 1 | 0 | 1 | 0 | 0 |
| 6 | 1 | 1 | 1 | 1 | 0 | 0 | 1 | 1 | 0 | 1 | 0 |
| 7 | 1 | 1 | 0 | 1 | 1 | 0 | 0 | 1 | 1 | 0 | 0 |
| 8 | 1 | 1 | 0 | 0 | 1 | 1 | 1 | 0 | 0 | 0 | 0 |
| 9 | 1 | 0 | 0 | 0 | 0 | 1 | 1 | 1 | 1 | 0 | 0 |
| - | 0 | 0 | 0 | 0 | 0 | 0 | 0 | 0 | 0 | 0 | 0 |
| BLANK | 0 | 0 | 0 | 0 | 1 | 0 | 0 | 0 | 0 | 0 | 1 |
| E | 1 | 0 | 1 | 1 | 1 | 0 | 1 | 1 | 0 | 1 | 0 |

4,000,565

DIGITAL AUDIO OUTPUT DEVICE

FIELD OF THE INVENTION

This invention relates to input to output conversion apparatus for signals and in particular to devices for aiding visually handicapped persons by making audible the character information of visible, but silent, displays.

PRIOR ART

Reading devices for blind or visually handicapped persons have long been a subject of investigation. The usual approach is to make some sort of a scanner or hand held wand or other equipment for recognizing the optical displays. Some of these devices have included means for converting the optical displays to audible tones. The tones, in turn, are useful to the visually handicapped users. Some devices convert the input signals to drive physical stimulators. For example, U.S. Pat. No. 3,676,938 shows a reading device and U.S. Pat. No. 3,800,082 actually can produce an "auditory image" of two-dimensional patterns. Similarly, U.S. Pat. No. 3,229,075 is directed to a hand held wand or reading device. U.S. Pat. Nos. 2,582,728 and 2,487,511 utilize tone variations as their output to indicate contours and objects in general. U.S. Pat. Nos. 3,359,425 and 2,615,992 also convert optical displays to audible tones.

A good deal of work was done in connection with the well-known "Optiphone" shown in U.S. Pat. No. 3,007,259 which transforms ordinary printed matter into recognizable auditory signals. All of the prior art mentioned thus far shares a common characteristic, however, in that the audible output is in analog form and requires considerable experience and training on the part of the operator before reading can be accomplished.

Analogous to this problem are devices for the blind and/or for persons who cannot, due to other factors, permit their attention to be distracted from what they are presently looking at, but who nevertheless need a signal indicative of the state of a display. For example, U.S. Pat. No. 3,828,252 shows a meter with an audible readout. In it, words which can be easily recognized are audibly read out from a record as selected by an electronic selection means which synchronizes the read out to create an actual message. This patent, intended for the use of the blind or visually handicapped people, is directed towards applications where digital optical displays are to be read out for blind persons. The digital values of the display are converted into selection signals for the recorded words on selected tracks or locations in a storage medium and are then played back in sequence.

Other audible indicators such as those in U.S. Pat. No. 3,823,383 are directed toward providing a warning signal or audible indication which is useful to both sighted and unsighted persons. Automatic signallers for weighing devices, such as those in U.S. Pat. Nos. 2,383,321, 2,400,277 and 2,456,062 are examples.

The foregoing audio indicator devices may be generally characterized in that they are either too simple to convey more than a single item of information, i.e., overweight and underweight indicators, or they are so complex, i.e., converters for converting symbols into spoken words, etc., that they cannot be readily made available at a low price to the handicapped person, due primarily to the necessity of converting the signals to an analog output in the form of spoken words.

OBJECTS OF THE INVENTION

In light of the aforementioned difficulties and shortcomings in the prior art, it is an object of this invention to provide an improved, digitally coded, tone output enunciator for visible displays.

Another object of the invention is to provide an improved means for adapting digital visual display apparatus for use by blind or visually handicapped persons.

SUMMARY OF THE INVENTION

The foregoing and other objects of the invention are met by providing an electronic conversion apparatus which takes the output from a visual display, serially by character, and converts the serial characters into serially enunciated tone codes according to a given code format which is then reproduced through an output transducer so that the audible tones may be understood by the user.

The foregoing and other objects, features and advantages of the invention will be apparent from the following more particular description of a preferred embodiment of the invention as illustrated in the accompanying drawings.

BRIEF DESCRIPTION OF THE DRAWINGS

FIG. 4 illustrates the tone code truth table for converting the optical display to audible tones.

Figure 1A:
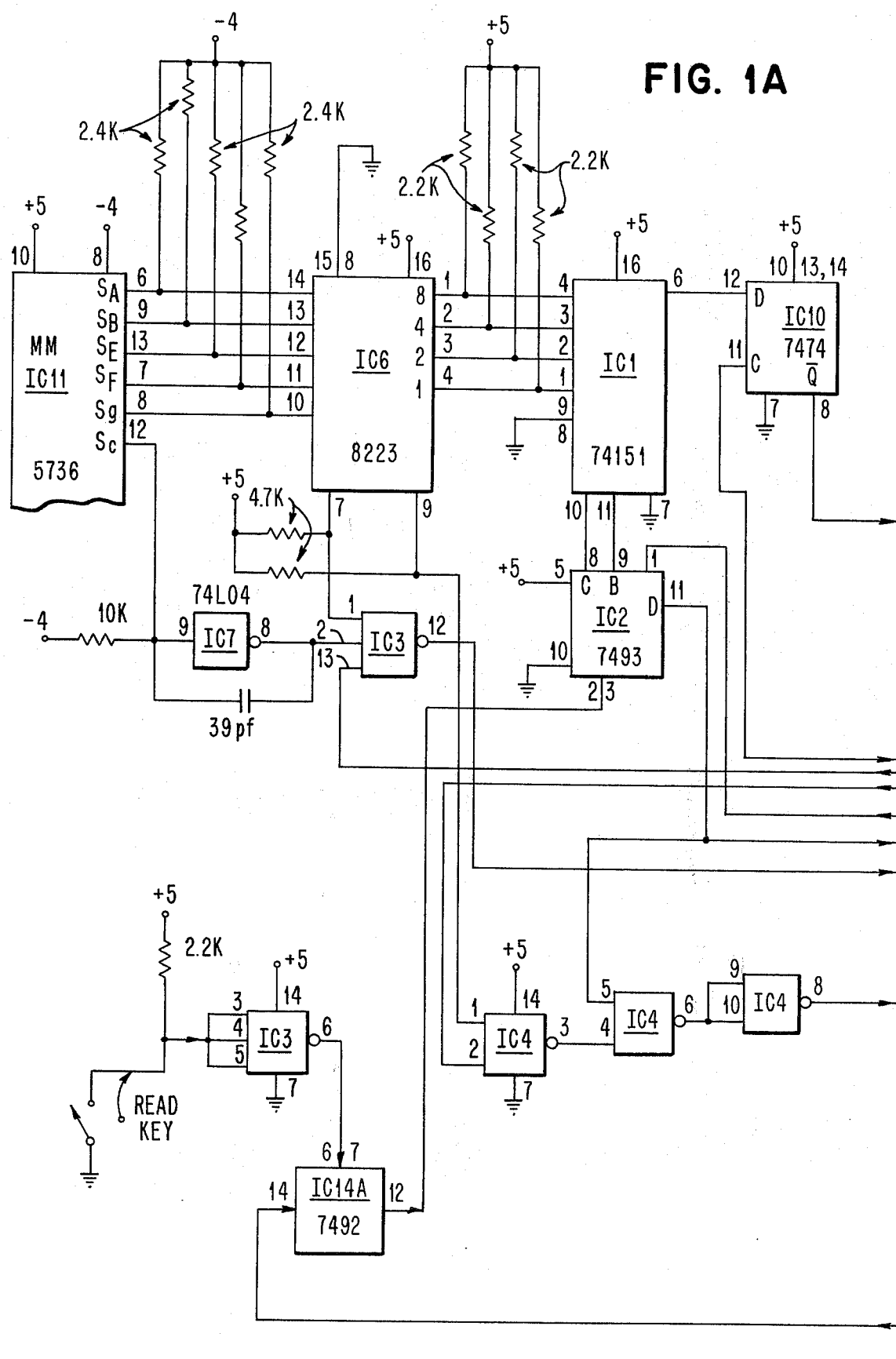
FIGS. 1A through 1C illustrate, in block schematic form a preferred embodiment of the invention as applied to an electronic hand held calculator, or other source of digital visual data, the optical display of which is to be audible enunciated to the user.

The basic elements of the preferred embodiment are a source of digital visual data and a means to convert the optical digital data into audible digital coded data. The coding may be by tone, for example. In the preferred embodiment, an electronic calculator (of a well-known commercially available sort) has connected to it a converter for converting the optical character displays into binary coded decimal (BCD) data form which is then reproduced serially on a two tone audio oscillator which is controlled by means of a scanner.

The scanner selects the character to be "read" which is then reproduced in audible form serially by bit through the two tone oscillator. For simplicity, if the data bit being read is a logical 0, the output tone is low, and if the data value is a logical 1, the output tone is high. The selection of high and low designations is arbitrary and might easily be reversed if desired.

The high and low tones enable the user to distinguish between values of successive bits and a short pause occurs between the bits in the output tones to allow the user to recognize the separation between successive bits (especially if the successive bits were identical, i.e., both high or low). The user is able to distinguish between numbers by a pause which is equal to, or longer than, the ordinary playback or readout time for a given number or character in the optical display. The output sequence of each number or character in the display is arbitrary, but the preferred embodiment uses an 8, 4, 2, 1, sequence as opposed to 1, 2, 4, 8, sequence. It will be appreciated that four bits in B C D code can represent sixteen different characters, each with its own unique tone sequence of high and low tones in groups of four sequential high-low tone groups.

In the present embodiment, the numerals 0 through 9, a minus sign, an error signal, a decimal point, and other significant numerals or characters would all be encompassed within the sixteen character tone code set provided by four bit B C D tone code groups. It is apparent that if it is desired to represent a greater variety of optical characters, the tone code groups could be expanded to five, six, or more bits as necessary. Since, however, numerals are usually read sequentially from left to right and one at a time, the four bit tone code B C D groups are most advantageous where numerals are being read out for use by an operator. For example, if a numeral displayed happened to be 917, its representation in audible B C D tone code in high and low tones (with high and low designating 1 and 0 as previously indicated) would be as follows: HLLH, pause, LLLH, pause, LHHH.

The high tone chosen in the present embodiment is arbitrary, but was found to be more pleasing at about 860 Hz. The low tone chosen was about 460 Hz and the length of a pause between sequential tones was approximately 100 milliseconds with the pause between tone code groups for each numeral being approximately 300 milliseconds. A variable speed control has also been implemented to allow an individual user to vary the readout speed.

In the present embodiment, the minus sign is read out as four high tone intervals. The specific embodiment shown uses a calculator chip which does not have a decimal point indication. If the instrument did have a decimal point, the decimal point could be inserted as a character having a continuous tone interval instead of four tone intervals, such as the type that is used for numbers. Alternatively, the decimal could be given a unique four tone code, but it is easier for some users to recognize the continuous tone instead.

User feedback is provided in a preferred embodiment by providing a short tone output each time a key is depressed. An error condition which may occur in using the electronic calculator is used to generate a continuous tone (not a continuous tone interval such as is used to indicate a decimal point, for example, but a continuous unending tone) which can only be stopped by clearing, resetting, etc.

Turning then, to FIG. 1A, a preferred embodiment is illustrated in conjunction with a six digit electronic calculator chip in the form of an integrated circuit. The specific integrated circuit chip utilized is a National Semiconductor Model MM5736, which is packaged in a standard eighteen pin dual in line housing. This chip, designated as IC11 in the drawings, provides as a standard output a seven segment optical display drive cord for use with a typical Light Emitting Diode matrix, (LED) display. The seven segment drive code is converted to binary coded decimal from using a Signetic's Model 8223 Field Programmable Read-Only Memory identified as IC6 in the drawings. It is a 256 bit read-only memory organized as 32 eight-bit words. The words are selected by five binary address lines and full word decoding is incorporated on the chip. FIG. 4 shows the truth table utilized in the present invention for converting the inputs to IC6 into B C D outputs.

Figure 1B:
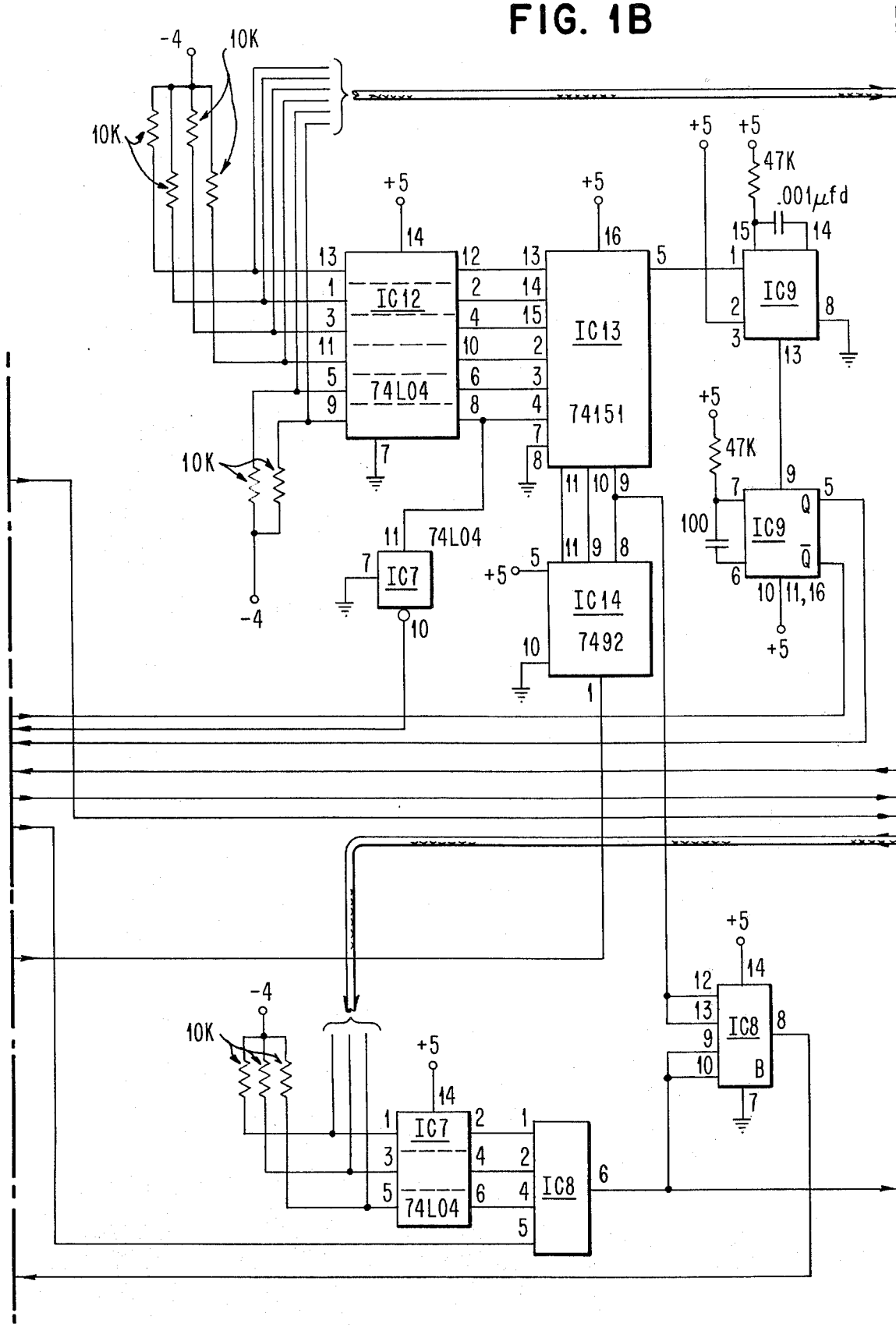
Figures 1, 1C:
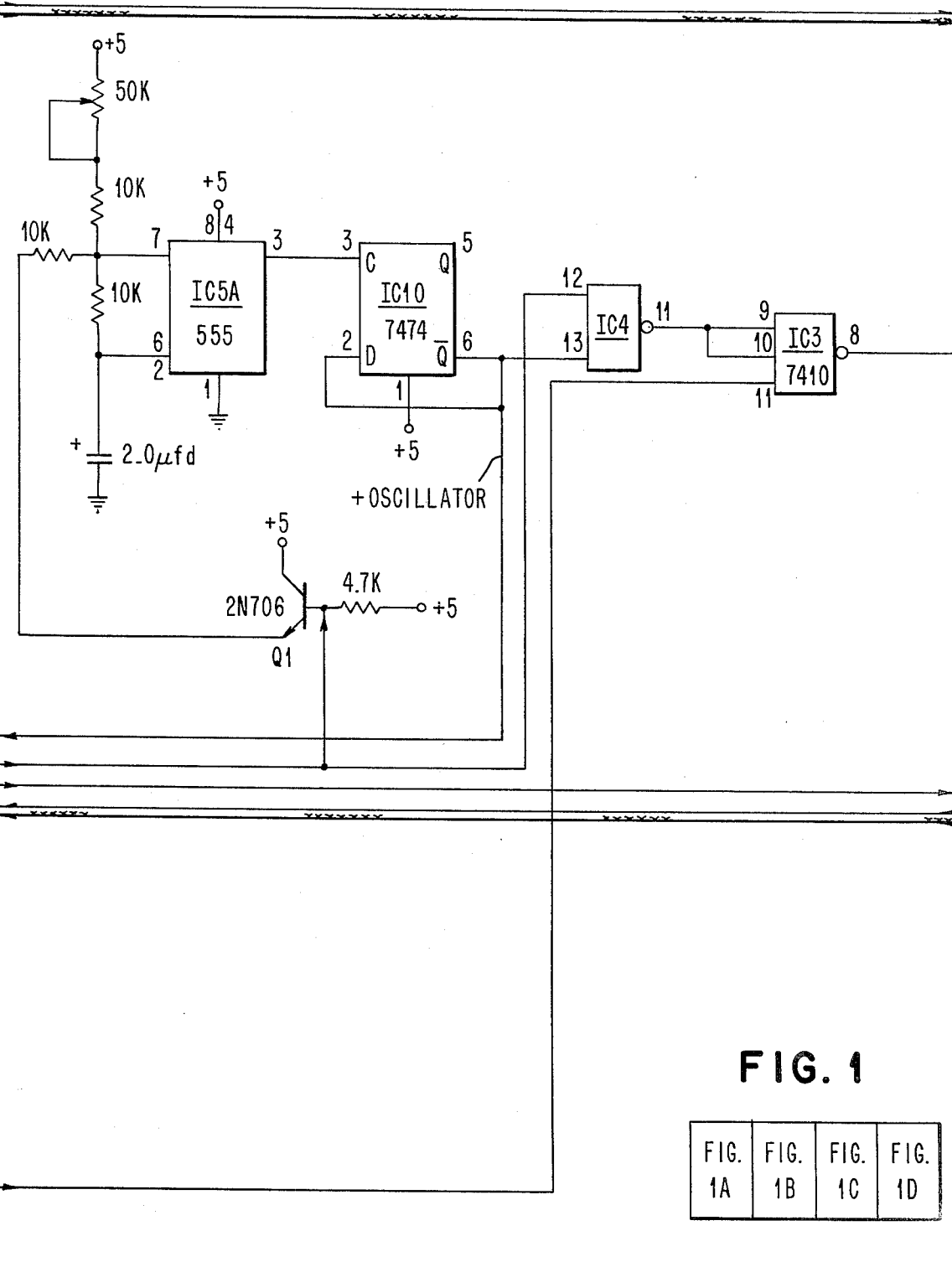
Turning now to FIG. 1, a preferred embodiment of the invention as applied to any convenient source of digital optical data such as, in the preferred embodiment, a hand held electronic calculator display. Other devices which provide similar digital outputs are digital multimeters, digital clocks, digital readout frequency generators, volt meters, or even printer devices, etc., as is well known.
Figure 1D:
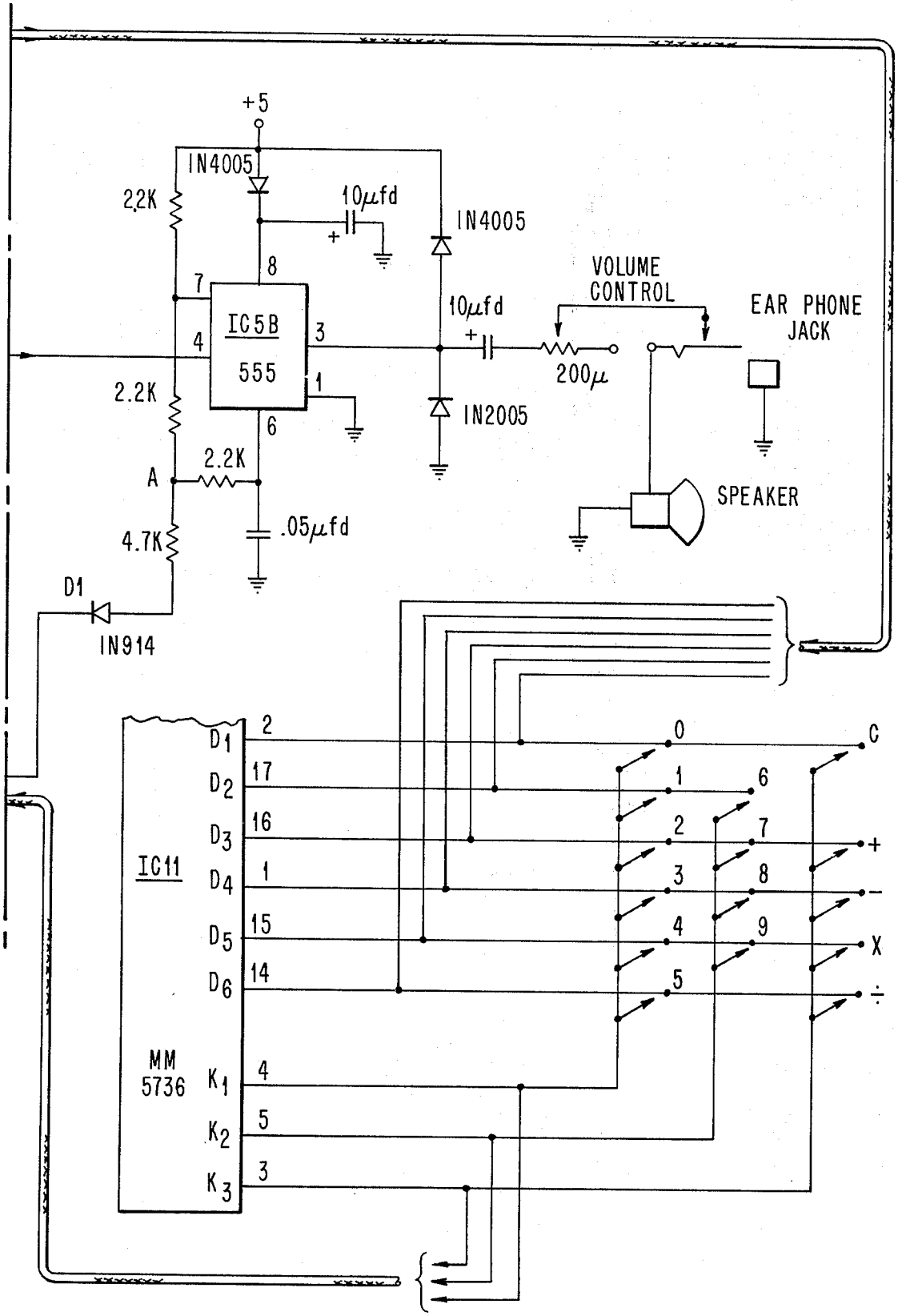

The digit drive lines from calculator chip IC11 in FIG. 1C are electrically interfaced with the rest of the circuitry by integrated circuit 12, which is a series of inverters, commercially available as a Model SN74L04 Texas Instruments chip (Model SN74L04N) was utilized in the preferred embodiment). It will be noted from the truth table in FIG. 4 that the digit six and the error E display utilize the same decode signals. In order to prevent confusion, IC7 and IC3, pins 8 and 9 and pins 1, 2, 12 and 13, respectively, on these chips are utilized to signal the E display character which occurs when the calculator chip IC11 has an error condition. IC7 is another Texas Instrument Model SN74L04N and IC3 is a Texas Instrument Model SN7410 triple 3 input positive — NAND gate circuit.

The two tone oscillator used in the present invention is implemented on integrated circuit 5B which is a Signetic's Model 555 (as is IC5A). IC5B is a two tone oscillator which is utilized to drive ear phones or other suitable transducers such as a loud speaker. IC3, the previously mentioned triple 3 input positive NAND gate through its pins 8, 9, 10 and 11 is a negative OR function which turns on the oscillator in chip IC5B. The frequency of the oscillator is varied by changing the input through diode D1 to effectively change the RC time constant in the frequency circuit.

The scanner is embodied in integrated circuit 5A which comprises a primary oscillator which establishes the length of the tones and pauses. The oscillator in IC5A is made variable to allow for setting the pause between characters from about 100 milliseconds to about 2000 milliseconds as desired by the operator. This is accomplished through transistor Q1 which sets the time for the duration between groups of tones. Integrated circuit 10 through its pins 2, 3, 5, and 6, buffers the output of integrated circuit 5A and also divides the output by two. This provides the output which is used as the master clock signal in the preferred embodiment. Integrated circuit 10 is a Texas Instrument's Model SN7474, a dual D type positive edge trigger flip-flop circuit package.

Integrated circuits 1 and 2 are utilized to form a scanner for selecting the particular bit in the tone code which is to be reproduced. Integrated circuits 13 and 14 (Texas Instrument's part No. 74151 and No. 7492, respectively) select which digit is to be displayed, starting with the most significant and ending with the least significant digit. Integrated circuits 1 and 2 are Texas Instrument's Models SN74151 and SN7493, respectively. The SN74151 is a data selector or multiplexor which can be utilized to select one of eight different data sources according to the control levels put on the inputs. A more detailed description of the circuit embodiments in FIGS. 1A through 1C will now be given, together with an example of operation of the circuit.

It will be assumed that the operator has already keyed in to the calculator (by means of touch and knowledge of the location of the various key denominations) the problem to be solved. Next, read key 1 in FIG. 1A is depressed. This closes a switch which grounds the input through pins 3, 4, and 5 to integrted circuit IC3. This causes the output pin 6 of IC3 to go positive to provide an input on pins 6 and 7 to IC14A, which is the selector drive. IC14A provides an output on pin 12, which enables IC2, on pins 2 and 3. IC2 is a divide-by-eight counter which receives clock pulses on its pin 1 and which provides divided-by-two and divided-by-four outputs on pins 8 and 9 which are supplied to IC1 at pins 10 and 11. Another output from IC2 is at pin 11 where a divided-by-eight clock signal is produced.

IC1 is the selector or multiplexor which selects one of its inputs on pins 1, 2, 3, or 4 in response to the state of the input on pins 10 and 11, which are connected to IC2. IC2 counts clock pulses and produces divided-by-two, divided-by-four, and also divided-by-eight outputs. At the same time, IC13, pin 5, provides the output from the most signficant digit position, D6, from IC11 (the calculator chip) through an inverter IC12 which acts as an electrical interface. IC9, a Texas Instrument's No. 74123, delays the output from pin 5 of IC13 for approximately 10 microseconds and develops a 100 nanosecondstrobe at the end of the delay period. Pin 11 of IC2, the high order bit of the counter, is negative and this allows IC5A to run at its adjustable low speed. At the same time the output of IC5A is inputted to IC10 which divides it by two and provides a buffering function. The output of IC10 at pin 6 (the plus oscillator signal) causes IC2 to count as previously indicated.

When IC2 counts up to 4 (1, 0, 0, in binary), pin 11 of IC2 goes positive which turns on transistor Q1 and forces IC5A into fast operation. It also enables IC4, pin 12, and IC14, pin 5. If the digit being read (D6) is blank, IC6 pin 9 goes positive, enabling IC4 pin 1. The 100 nanosecond strobe pulse from IC9 causes a down level in IC14 which steps the counter in IC14 to the next digit and the data multiplexor of IC13 will then select in the next digit position for reading. If the next digit position is also blank, the above steps are repeated until a non-blank digit is detected.

When the oscillator at pin 13 of IC4 goes positive, the output goes negative and the output of pin 8 on IC3 goes positive which turns on IC5B (the tone oscillator) to produce a tone from the speaker or through the head phones. The frequency of the tone, indicative of a one or zero digit being read, is controlled as follows:

When the count in IC2 is 1, 0, 0 in binary, pin 1 of IC6 (the programmable read-only memory), which is the eight's position bit of the BCD value for the particular bit digit being read, is gated to pin 12 of IC10. Then the 100 nanosecond strobe from IC9 loads the eight's position BCD bit value into the latch of IC10.

The input to IC10 goes to an "up" level as 1 is read out from the selected input line at the multiplexor IC1. The $\overline{Q}$ output on pin 8 of IC10 will then go low. This is the frequency shift tone control for the tone oscillator in integrated circuit 5B. The output from pin 8 of IC10 is applied to lower the bias on diode D1 which will lower the voltage at the node A which lowers the threshold voltage on pins 2 and 6 of IC5B and causes the oscillator to oscillate more rapidly and provide a higher frequency tone at its output on pin 3.

If, on the other hand, the IC1 selects a 0 at one of its inputs, the output on pin 6 thereof will go to a low level and the output from IC10 at pin 8 will go high causing an increase subsequently in the node voltage at node A which will raise the threshold on the oscillator 5B which will lower the frequency of oscillation thereof and provide a lower tone at the output on pin 3.

If the calculator chip IC11 activates its output pin $S_c$ on the segment drive portion of the digital display output, an E signal or error indication has been generated by the calculator. This output is inverted in inverter IC7 and applied as one input on pin 2 to an NAND gate on IC3. The other inputs to IC3 are the error code output from the programmable read-only memory in IC6 (on pin 7 thereof) together with the digit 6 output time coming on line B2 from the inverter IC7 pin 10 which takes the output from the keyboard drive portion of the calculator chip at the time the sixth drive line for the keyboard of the calculator is driven positive. This is done because, in the programmable read-only memory IC6, the decode for the numeral 6 and for the error E signal are the same. Therefore, if the keyboard is not then being driven, but the error condition signal in on and an error decode from the programmable read-only memory IC6 has occurred a true error has occurred. If, however, output pin 12 of the calculator chip IC11 is not being driven, the NAND gate of IC3 will not be activated and a no error signal will be applied to an AND gate in IC8, a Texas Instrument's No. 7421, at pin 5 thereof. A "no error" signal is normally an up level which is applied to pin 5 of the AND gate in IC8 as shown. The other inputs are normally at an up level so long as no keys are depressed which would cause an up level on inputs 1, 3, or 5 of inverter 7 whose outputs 2, 4, and 6, respectively, are connected to inputs 1, 2, and 4 of the AND gate 8. Then an up level is normally provided on the output pin 6 of IC8 which indicates that no key is down nor is there any error detected.

If any key is depressed or if an error is indicated, pin 6 of IC8 will go negative, pins 9 and 10 of IC8 will go negative and pin 8 of IC8 will go negative. The negative going signal from pin 8 of IC8 will cause IC14A, pin 14 to go negative which will cause pin 12 of IC14A to go to an up level which will reset the counter IC2. Also, the negative going signal from pin 6 of IC8 goes to pin 11 of IC3 which causes IC5B to be turned on as long as the error condition exists or the key is depressed which produces a continuous output tone to alert the operator that such an event is occurring.

Counter IC14 counts digits as they as read out. After the sixth (or the last) digit, pin 8 of IC14 will go negative. This negative going signal causes pins 12 and 13 of IC8 to go negative which causes counter IC2 to reset as occurred previously with pins 9 and 10 of IC8. Resetting counter IC2 by whatever means, stops multiplexor IC1 from scanning the tone code output from IC6. Under normal operation, however, AND gates 8 and 8B in IC8 will normally be fully activated and an up level will be present at their outputs at pins 6 and 8, respectively, so that activity will not be stopped and so that the NAND gate 3 at pin 8 will have a normal low level output connected to pin 4 of oscillator 5B. If an up level were present on this pin, the oscillator would be continuously on and a continuous tone would be present. It is also apparent that if any key is depressed, AND gate 8 will have one of its pins driven to a minus level which will cause disabling of AND gate 8 and will produce a low level output at pin 6 thereof which will provide a key down, or low level signal, to NAND gate 3, pin 11. At the same time, pins 9 and 10 thereof may be in any state and for so long as the key button is held down, a tone will be produced since the output of NAND gate 3 will be up and it is connected to pin 4 of the oscillator 5B.

A divide-by-eight clock signal is applied (via IC4) to input pin 1 of IC14 which is a counter used to divide by six. Its outputs are connected to IC13 which is the data selector which selects which of the drive lines D1 through D6 in the calculator IC11, whose plus 5 volt output level is applied to an inverter in IC12 to create a low level output. The selected input line from the multiplexor IC13 is applied at its output in 5 which provides an input to the control pin 1 of single shot IC9. Thus, if the calculator chip IC11 is in the process of driving the selected drive line, a down going pulse at the output of multiplexor 13 will be present and single shot IC9 will be activated and its pin 13 will go to an up level. This is applied to a second single shot IC9 as shown, and will drive the Q output on pin 5, which is the strobe signal. The strobe signal is applied to pin 2 of a NAND gate in IC4, a Texas Instrument's part No. 7400. The outer input to the NAND gate is maintained at an up level by a connection to a source of voltage to a load resistor and the output of pin 9 of IC6 which is positive if the display driver is not blank at the digit position selected. Thus, when the strobe signal arrives at pin 2, it will be positive. The output from pin 3 will be applied to the input, pin 4 of another NAND gate in IC4. Pin 5 of this latter NAND gate is activated by the clock pulse as well, so if either pin 4 or pin 5 is at the down level, an up level output at pin 6 will be produced. This is inverted by another NAND gate with its inputs 9 and 10 wired together so that a down level at pin 8 from IC4 is produced. This level is applied to IC14 pin 1 to cause the counter to increment by one count and to drive the data selector IC13 to the next step.

Figure 2:
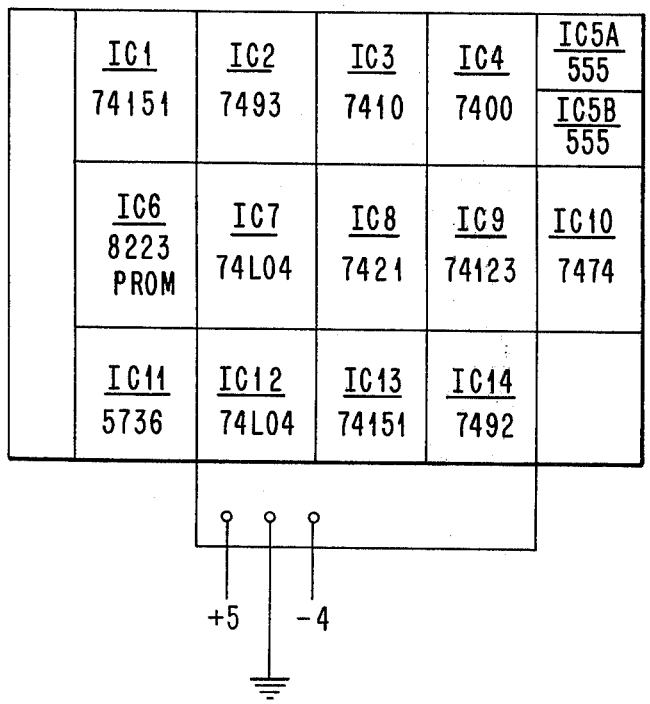
FIG. 2 is a plan view of a circuit card which carries a number of integrated circuit packages in which the embodiment of FIGS. 1A through 1C is implemented.

The integrated circuits, IC1 through 14 are standard, commercially available items, well-known in the art and would be identified and laid out on a circuit board as illustrated by FIG. 2. Any convenient power supply giving the voltages shown in FIG. 2 would then be connected to the various opertive pin numbers as shown in the drawings of FIG. 1. The values of resistors, capacitors and the designation of any transistors or diodes are given in the figures and will not be repeated, it being obvious to one of ordinary skill what the elements are and what their purpose is.

The operation of the tone output device during one cycle for a readout is as follows:

The read key is depressed and pin 6 of IC3 goes positive, resetting IC14A. IC14A, pin 12 goes negative, thus enabling IC22 to start counting.

The counter IC2 will count in binary 100, 101, 110, 111 and will gate out the eight, four, two and one bit positions in BCD code from IC6. When IC2 counter returns to a count of 000, the fall of the high order bit causes IC14 to advance its count and to select the next digit.

When IC14 finally returns to a count of 000, IC14A is turned on via IC8 pin 8, 12 and 13 which stops the readout.

If the E character is detected at any character position, IC14 is turned on via IC8 pin 8, 9, and 10 which stops the readout and causes IC5B, the tone oscillator, to turn on each time the E is detected.

For the operator's convenience, each time any calculator key is depressed, IC14A is turned on to stop the readout and to cause a tone output through the oscillator IC5B at every D6 drive time for as long as the key is held depressed.

Figure 3:
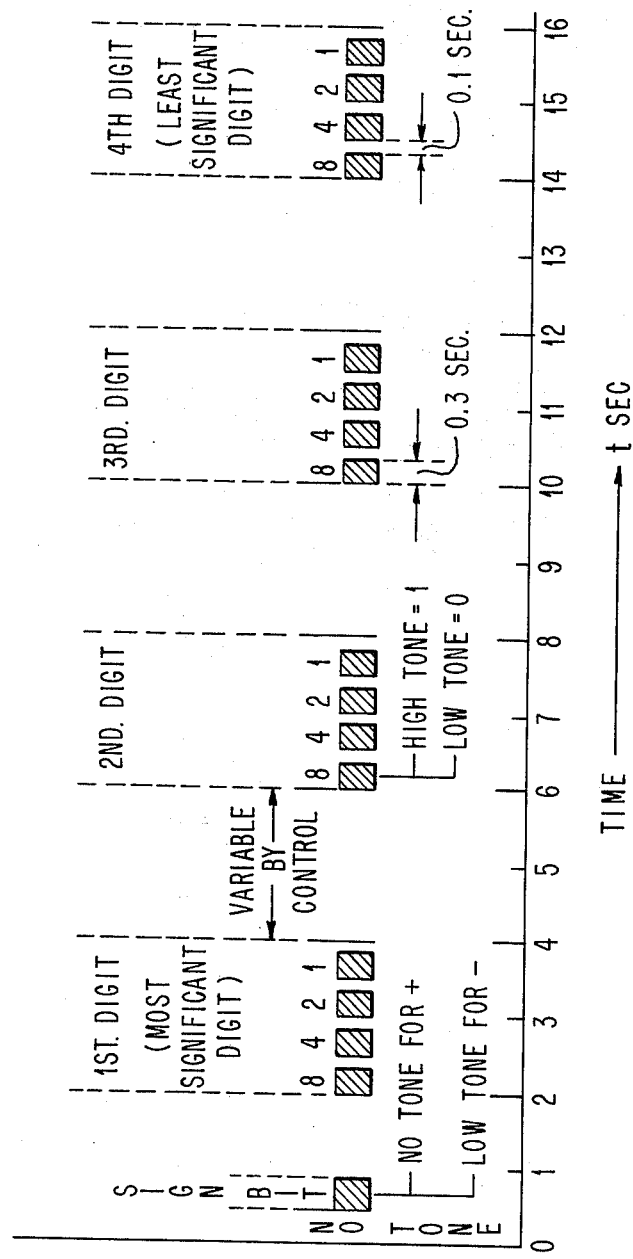
FIG. 3 is a schematic timing chart which illustrates the operation of the preferred embodiment.

FIG. 3 illustrates in a schematic form an operation for a timing chart reading out four bits BCD from left to right. Beginning at the left-hand edge of FIG. 3, there is initially no tone or other indication until the read key is depressed. When the read key is depressed, a low tone is produced for indicating a negative sign and no tone is produced at all for a positive sign, although it is obvious that a high tone could be produced for this if desired. There then follows a pause and then a group of four tones will be serially produced for the first digit in the BCD code scheme of the display which is being read out. Each individual tone lasts for approximately 300 milliseconds in the preferred embodiment, but this could be varied at will. A short pause of approximately 100 milliseconds is interspersed between individual tone bursts. A high tone has been arbitrarily chosen to indicate a one in the bit position 8, 4, 2, or 1 BCD code and a low tone to indicate a zero is the bit position 8, 4, 2, or 1 thereof. Following the readout of the most significant digit as four tones, a pause of approximately as long as the total time to read out four bits ensues and then the second digit in the display is read out, etc. The total time in seconds to read out four decimal digits in BCD tone code in the example shown is approximately sixteen seconds. While this is a relatively long period of time, a speed control is included in the circuit in FIG. 1 to reduce the gap or pause between the series of tones between the first digit and the second, etc., so that the time can be cut nearly in half or extended, if desired.

While the invention has been particularly shown and described with reference to a preferred embodiement thereof, it will be understood by those skilled in the art that various changes in form and details may be made therein without departing from the spirit and scope of the invention.

What is claimed is:

1. Apparatus for converting silently displayed visual data characters into serially sequenced, tone coded audible data signals, at a rate of presentation between and duration of said serially sequenced tones to be auditorially intelligible to humans, comprising:

a source of first electrical drive signals of the type for operating a visual data display means;

converting means connected to said source of first electrical drive signals for converting said first electrical drive signals into serially sequenced and tone coded second electrical drive signals;

tone signal rate control means and tone signal duration control means connected to said converting means for controlling the rate and duration of said second electrical drive signals to produce a rate of presentation and duration of said signals to be auditorially intelligible to humans; and transducer means connected to said converting means to receive said serially sequenced and tone coded second electrical drive signals for audibly and serially producing tones corresponding in frequency, rate and duration to said sequenced and tone coded second electrical drive signals.

2. Apparatus as described in claim 1, wherein:

said source of said first electrical drive signal comprises an optical data display means wherein said first electrical signals are the optical data display control signals therefor; and said means for converting said first electrical drive signals into said serially sequenced and tone coded second electrical drive signals comprises a readable memory device connected to have its memory addressed by said first electrical drive signals and which has said serially sequenced and tone second electrical drive signals stored at locations which correspond to said first electrical drive signals.

3. Apparatus as described in claim 2, wherein:

said optical data display means is a segmented, selectively illuminable array of visible areas which are selected to form segmented data characters in correspondence with said first electrical drive signals; and said means for converting said first electrical drive signals into said serially sequenced and tone coded second drive signals further comprises means for sequentially outputting serial elements of said memory location contents addressed by said first electrical drive signals.

4. Apparatus as described in claim 3, wherein:

said means for converting said first electrical drive signals into said serially sequenced and tone electrical drive signals further comprises means for sequentially applying said first electrical drive signals to said memory device in sequence by character from said data display means.

5. Apparatus as described in claim 4, wherein:

said optical data display means comprises at least one, seven-segment, selectively illuminable character display means; and said means for converting said first electrical drive signals into said serially sequenced and tone coded second electrical drive signals contains BCD coded memory location contents.

* * * * *

UNITED STATES PATENT AND TRADEMARK OFFICE
CERTIFICATE OF CORRECTION

PATENT NO. : 4,000,565
DATED : January 4, 1977
INVENTOR(S) : Albert W. Overby and Donald P. Parks It is certified that error appears in the above-identified patent and that said Letters Patent are hereby corrected as shown below:

Claim 2, Column 9, line 2, after "tone" insert --coded--; and

Claim 4, Column 10, line 3, after "tone" insert --coded second--.

Signed and Sealed this

Nineteenth Day of April 1977

[SEAL]

Attest:

RUTH C. MASON
Attesting Officer

C. MARSHALL DANN
Commissioner of Patents and Trademarks